(12) United States Patent
Stubbs et al.

(10) Patent No.: US 8,306,630 B2
(45) Date of Patent: Nov. 6, 2012

(54) APPARATUS TO SELECTIVELY INCREASE MEDICAL DEVICE LEAD INNER CONDUCTOR INDUCTANCE

(75) Inventors: Scott R. Stubbs, Maple Grove, MN (US); Jeffrey E. Stahmann, Ramsey, MN (US); Arthur J. Foster, Centerville, MN (US); Ronald W. Kunkel, Jim Falls, WI (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 59 days.

(21) Appl. No.: 12/905,336

(22) Filed: Oct. 15, 2010

(65) Prior Publication Data

US 2011/0160816 A1   Jun. 30, 2011

Related U.S. Application Data

(60) Provisional application No. 61/291,114, filed on Dec. 30, 2009.

(51) Int. Cl.
*A61N 1/05*   (2006.01)
(52) U.S. Cl. ....................................................... 607/116
(58) Field of Classification Search .................... 607/116
See application file for complete search history.

(56) References Cited

U.S. PATENT DOCUMENTS

| | | | |
|---|---|---|---|
| 5,003,975 A | 4/1991 | Hafelfinger et al. |
| 5,201,865 A | 4/1993 | Kuehn |
| 5,259,394 A | 11/1993 | Bens |
| 5,370,666 A | 12/1994 | Lindberg et al. |
| 5,476,485 A | 12/1995 | Weinberg et al. |
| 5,534,018 A | 7/1996 | Wahlstrand et al. |
| 5,549,646 A | 8/1996 | Katz et al. |
| 5,727,552 A | 3/1998 | Ryan |
| 5,727,553 A | 3/1998 | Saad |
| 5,755,742 A | 5/1998 | Schuelke et al. |
| 5,766,227 A | 6/1998 | Nappholz et al. |

(Continued)

FOREIGN PATENT DOCUMENTS

DE   3032317   3/1981

(Continued)

OTHER PUBLICATIONS

International Search Report and Written Opinion issued in PCT/US2010/052819, mailed Jan. 26, 2011, 12 pages.

(Continued)

*Primary Examiner* — Carl H Layno
*Assistant Examiner* — Yun Haeng Lee
(74) *Attorney, Agent, or Firm* — Faegre Baker Daniels LLP (57) ABSTRACT

A medical device lead includes an insulative lead body, outer and inner conductive coils, and a flexible core assembly. The outer conductive coil extends through the lead body and is coupled to a first electrode at a distal end of the outer conductive coil. The inner conductive coil extends coaxially with the outer conductive coil, is coupled to a second electrode at a distal end of the inner conductive coil, and includes a central lumen. The flexible core assembly is disposed in the central lumen and is comprised of a material that has a saturation magnetization of at least about 1.5 T and a relative permeability of greater than one. The flexible core assembly includes a positioning interface configured for manipulation of the flexible core assembly such that the flexible core assembly translates through the central lumen during insertion and extraction of the flexible core assembly.

18 Claims, 4 Drawing Sheets

U.S. PATENT DOCUMENTS

| | | | |
|---|---|---|---|
| 5,800,496 A | 9/1998 | Swoyer et al. | |
| 5,817,136 A | 10/1998 | Nappholz et al. | |
| 5,891,179 A | 4/1999 | Er et al. | |
| 6,016,447 A | 1/2000 | Juran et al. | |
| 6,101,417 A | 8/2000 | Vogel et al. | |
| 6,317,633 B1 | 11/2001 | Jorgenson et al. | |
| 6,721,600 B2 | 4/2004 | Jorgenson et al. | |
| 6,765,144 B1 | 7/2004 | Wang et al. | |
| 6,799,067 B2 * | 9/2004 | Pacetti et al. | 600/431 |
| 6,949,929 B2 | 9/2005 | Gray et al. | |
| 6,985,775 B2 * | 1/2006 | Reinke et al. | 607/116 |
| 6,999,818 B2 | 2/2006 | Stevenson et al. | |
| 7,013,180 B2 | 3/2006 | Dublin et al. | |
| 7,047,075 B2 | 5/2006 | Stubbs | |
| 7,047,083 B2 | 5/2006 | Gunderson et al. | |
| 7,050,855 B2 | 5/2006 | Zeijlemaker et al. | |
| 7,113,827 B2 | 9/2006 | Silvestri et al. | |
| 7,123,013 B2 | 10/2006 | Gray | |
| 7,135,978 B2 | 11/2006 | Gisselberg et al. | |
| 7,138,582 B2 | 11/2006 | Lessar et al. | |
| 7,174,219 B2 | 2/2007 | Wahlstrand et al. | |
| 7,174,220 B1 | 2/2007 | Chitre et al. | |
| 7,239,916 B2 | 7/2007 | Thompson et al. | |
| 7,289,851 B2 | 10/2007 | Gunderson et al. | |
| 7,369,898 B1 | 5/2008 | Kroll et al. | |
| 7,388,378 B2 | 6/2008 | Gray et al. | |
| 7,535,363 B2 | 5/2009 | Gisselberg et al. | |
| 2003/0083726 A1 | 5/2003 | Zeijlemaker et al. | |
| 2003/0140931 A1 | 7/2003 | Zeijlemaker et al. | |
| 2003/0144705 A1 | 7/2003 | Funke | |
| 2003/0144718 A1 | 7/2003 | Zeijlemaker | |
| 2003/0144719 A1 | 7/2003 | Zeijlemaker | |
| 2003/0144720 A1 | 7/2003 | Villaseca et al. | |
| 2003/0144721 A1 | 7/2003 | Villaseca et al. | |
| 2003/0204217 A1 | 10/2003 | Greatbatch | |
| 2004/0064161 A1 | 4/2004 | Gunderson et al. | |
| 2005/0113676 A1 | 5/2005 | Weiner et al. | |
| 2005/0113873 A1 | 5/2005 | Weiner et al. | |
| 2005/0113876 A1 | 5/2005 | Weiner et al. | |
| 2005/0149169 A1 | 7/2005 | Wang et al. | |
| 2005/0197677 A1 | 9/2005 | Stevenson | |
| 2005/0222656 A1 | 10/2005 | Wahlstrand et al. | |
| 2005/0222657 A1 | 10/2005 | Wahlstrand et al. | |
| 2005/0222658 A1 | 10/2005 | Hoegh et al. | |
| 2005/0222659 A1 | 10/2005 | Olsen et al. | |
| 2006/0030774 A1 | 2/2006 | Gray et al. | |
| 2006/0041294 A1 | 2/2006 | Gray | |
| 2006/0118758 A1 | 6/2006 | Wang et al. | |
| 2006/0247747 A1 | 11/2006 | Olsen et al. | |
| 2006/0247748 A1 | 11/2006 | Wahlstrand et al. | |
| 2006/0252314 A1 | 11/2006 | Atalar et al. | |
| 2006/0271138 A1 | 11/2006 | MacDonald | |
| 2007/0010702 A1 | 1/2007 | Wang et al. | |
| 2007/0027532 A1 | 2/2007 | Wang et al. | |
| 2007/0179577 A1 | 8/2007 | Marshall et al. | |
| 2007/0179582 A1 | 8/2007 | Marshall et al. | |
| 2007/0191914 A1 | 8/2007 | Stessman | |
| 2008/0033497 A1 | 2/2008 | Bulkes et al. | |
| 2008/0051854 A1 | 2/2008 | Bulkes et al. | |
| 2008/0132985 A1 | 6/2008 | Wedan et al. | |
| 2008/0154348 A1 | 6/2008 | Atalar et al. | |
| 2008/0188910 A1 * | 8/2008 | Spaide | 607/89 |
| 2008/0208290 A1 | 8/2008 | Phillips et al. | |
| 2009/0005825 A1 | 1/2009 | MacDonald | |
| 2009/0024180 A1 | 1/2009 | Kisker et al. | |
| 2009/0149920 A1 | 6/2009 | Li et al. | |
| 2009/0149933 A1 | 6/2009 | Ameri | |
| 2009/0204171 A1 | 8/2009 | Ameri | |
| 2009/0210022 A1 | 8/2009 | Powers | |
| 2010/0103215 A1 | 4/2010 | Iriguchi | |
| 2010/0106215 A1 | 4/2010 | Stubbs et al. | |
| 2011/0060394 A1 | 3/2011 | Poore | |
| 2011/0087302 A1 | 4/2011 | Ameri | |

FOREIGN PATENT DOCUMENTS

| | | |
|---|---|---|
| EP | 1852810 B1 | 11/2007 |
| WO | WO2010078552 A1 | 7/2010 |

OTHER PUBLICATIONS

Basso, Christophe, "SPICE Model Simulates Spark-Gap Arrestor", Electronics Design, Strategy, and News (EDN), Jul. 3, 1997, 4 pages.

File History for U.S. Appl. No. 11/015,807, filed Dec. 17, 2004.

International Search Report and Written Opinion issued in PCT/US2009/056843, mailed Dec. 29, 2009, 13 pages.

International Search Report and Written Opinion issued in PCT/US2010/048620, mailed Apr. 5, 2011, 10 pagaes.

Partial International Search Report issued in PCT/US2011/052541, mailed Dec. 6, 2011, 4 pages.

* cited by examiner

APPARATUS TO SELECTIVELY INCREASE MEDICAL DEVICE LEAD INNER CONDUCTOR INDUCTANCE

CROSS-REFERENCE TO RELATED APPLICATION

This application claims priority to Provisional Application No. 61/291,114, filed Dec. 30, 2009, which is herein incorporated by reference in its entirety.

TECHNICAL FIELD

The present invention relates to implantable medical devices. More particularly, the present invention relates to a flexible core insertable into the lumen of an inner lead conductor to increase the inductance of the inner lead conductor during an MRI procedure.

BACKGROUND

Magnetic resonance imaging (MRI) is a non-invasive imaging procedure that utilizes nuclear magnetic resonance techniques to render images within a patient's body. Typically, MRI systems employ the use of a magnetic coil having a magnetic field strength of between about 0.2 to 3 Teslas. During the procedure, the body tissue is briefly exposed to RF pulses of electromagnetic energy in a plane perpendicular to the magnetic field. The resultant electromagnetic energy from these pulses can be used to image the body tissue by measuring the relaxation properties of the excited atomic nuclei in the tissue.

During imaging, the electromagnetic radiation produced by the MRI system may be picked up by implantable device leads used in implantable medical devices such as pacemakers or cardiac defibrillators. This energy may be transferred through the lead to the electrode in contact with the tissue, which may lead to elevated temperatures at the point of contact. The degree of tissue heating is typically related to factors such as the length of the lead, the conductivity or impedance of the lead, and the surface area of the lead electrodes. Exposure to a magnetic field may also induce an undesired voltage on the lead.

SUMMARY

Discussed herein are various components for implantable medical electrical leads including a flexible magnetic core assembly that increases conductive coil inductance in the medical electrical leads to reduce transmission of MRI-induced energy to lead electrodes, as well as medical electrical leads including such components.

In Example 1, a medical device lead includes an insulative lead body, outer and inner conductive coils, and a flexible core assembly. The outer conductive coil extends through the lead body and is coupled to a first electrode at a distal end of the outer conductive coil. The inner conductive coil extends coaxially with the outer conductive coil, is coupled to a second electrode at a distal end of the inner conductive coil, and includes a central lumen. The flexible core assembly is disposed in the central lumen and is comprised of a material that has a saturation magnetization of at least about 1.5 T and a relative permeability of greater than one. The flexible core assembly includes a positioning interface configured for manipulation of the flexible core assembly such that the flexible core assembly translates through the central lumen during insertion of the flexible core assembly into the central lumen and extraction of the flexible core assembly from the central lumen.

In Example 2, the medical device lead according to Example 1, wherein the positioning interface is on a proximal end of the flexible core assembly.

In Example 3, the medical device lead according to either Example 1 or 2, wherein the positioning interface is configured for connection to a distal end of a guiding device that allows manipulation of the flexible core assembly via a proximal end of the inner conductive coil.

In Example 4, the medical device lead according to any of Examples 1-3, wherein the positioning interface includes a tapered opening sized to receive the distal end of the guiding device.

In Example 5, the medical device lead according to any of Examples 1-4, wherein the flexible core assembly is substantially cylindrical in an unflexed state.

In Example 6, the medical device lead according to any of Examples 1-5, wherein the flexible core assembly further includes a reinforcement member extending axially through the flexible core assembly.

In Example 7, the medical device lead according to any of Examples 1-6, wherein the flexible core assembly is comprised of a nanomagnetic material.

In Example 8, a medical device lead includes a conductive coil and a flexible core assembly. The conductive coil extends through a lead body and includes a proximal end, a distal end, and a central lumen. The flexible core assembly is disposed in the central lumen and is comprised of a material that has a saturation magnetization of at least about 1.5 T and a relative permeability of greater than one. The flexible core assembly includes a positioning interface configured for manipulation of the flexible core assembly such that the flexible core assembly translates through the central lumen during insertion of the flexible core assembly into the central lumen and extraction of the flexible core assembly from the central lumen.

In Example 9, the medical device lead according to Example 8, wherein the positioning interface is on a proximal end of the flexible core assembly.

In Example 10, the medical device lead according to either Example 8 or 9, wherein the positioning interface is configured for connection to a distal end of a guiding device that allows manipulation of the flexible core assembly via the proximal end of the conductive coil.

In Example 11, the medical device lead according to any of Examples 8-10, wherein the positioning interface includes a tapered opening sized to receive the distal end of the guiding device.

In Example 12, the medical device lead according to any of Examples 8-11, wherein the flexible core assembly is substantially cylindrical in an unflexed state.

In Example 13, the medical device lead according to any of Examples 8-12, wherein the flexible core assembly further includes a reinforcement member extending axially through the flexible core assembly.

In Example 14, the medical device lead according to any of Examples 8-13, wherein the flexible core assembly is comprised of a nanomagnetic material.

In Example 15, an assembly for increasing the inductance of a conductive coil in a medical device lead is positionable in a central lumen of the conductive coil. The assembly includes a flexible core comprised of a material that has a saturation magnetization of at least about 1.5 T and a relative permeability of greater than one. The assembly also includes a positioning interface coupled to a proximal end of the flexible core for manipulating the flexible core such that the flexible core translates through the central lumen during insertion of the flexible core into the central lumen and extraction of the flexible core from the central lumen.

In Example 16, the assembly according to Example 15, wherein the positioning interface is configured for connection to a distal end of a guiding device that allows manipulation of the assembly via the proximal end of the conductive coil.

In Example 17, the assembly according to either Example 15 or 16, wherein the positioning interface includes a tapered opening sized to receive the distal end of the guiding device.

In Example 18, the assembly according to any of Examples 15-17, wherein the flexible core assembly is substantially cylindrical in an unflexed state.

In Example 19, the assembly according to any of Examples 15-18, wherein the flexible core assembly further includes a reinforcement member extending axially through the flexible core assembly.

In Example 20, the assembly according to any of Examples 15-19, wherein the flexible core assembly is comprised of a nanomagnetic material.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
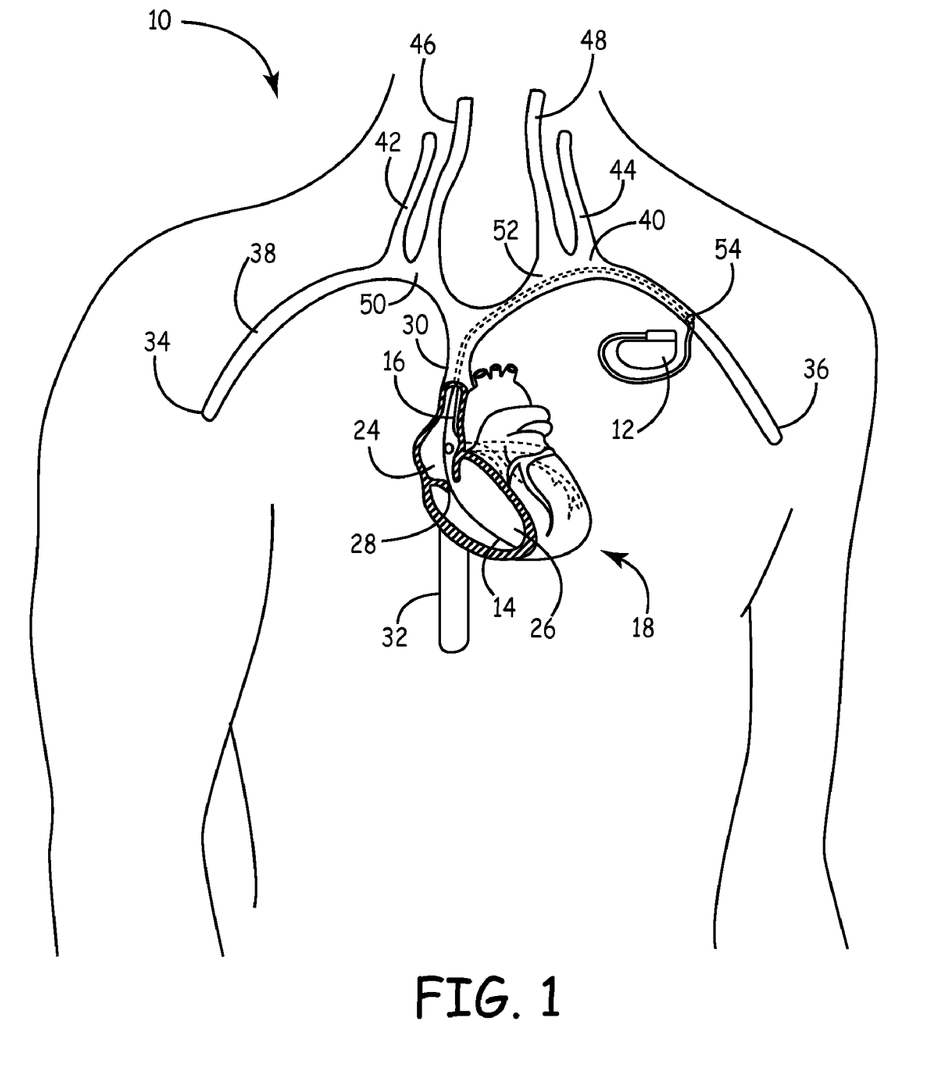
FIG. 1 is a schematic view of a cardiac rhythm management (CRM) system including a pulse generator and a lead implanted in a patient's heart according to an embodiment of the present invention.

FIG. 1 is a schematic view of a cardiac rhythm management (CRM) system 10 according to an embodiment of the present invention. As shown in FIG. 1, the CRM system 10 includes a pulse generator 12 coupled to a plurality of leads 14, 16 deployed in a patient's heart 18. As further shown in FIG. 1, the heart 18 includes a right atrium 24 and a right ventricle 26 separated by a tricuspid valve 28. During normal operation of the heart 18, deoxygenated blood is fed into the right atrium 24 through the superior vena cava 30 and the inferior vena cava 32. The major veins supplying blood to the superior vena cava 30 include the right and left axillary veins 34 and 36, which flow into the right and left subclavian veins 38 and 40. The right and left external jugular 42 and 44, along with the right and left internal jugular 46 and 48, join the right and left subclavian veins 38 and 40 to form the right and left brachiocephalic veins 50 and 52, which in turn combine to flow into the superior vena cava 30.

The leads 14, 16 operate to convey electrical signals and stimuli between the heart 18 and the pulse generator 12. In the illustrated embodiment, the lead 14 is implanted in the right ventricle 26, and the lead 16 is implanted in the right atrium 24. In other embodiments, the CRM system 10 may include additional leads, e.g., a lead extending into a coronary vein for stimulating the left ventricle in a bi-ventricular pacing or cardiac resynchronization therapy system. As shown, the leads 14, 16 enter the vascular system through a vascular entry site 54 formed in the wall of the left subclavian vein 40, extend through the left brachiocephalic vein 52 and the superior vena cava 30, and are implanted in the right ventricle 26 and right atrium 24, respectively. In other embodiments of the present invention, the leads 14, 16 may enter the vascular system through the right subclavian vein 38, the left axillary vein 36, the left external jugular 44, the left internal jugular 48, or the left brachiocephalic vein 52.

The pulse generator 12 is typically implanted subcutaneously within an implantation location or pocket in the patient's chest or abdomen. The pulse generator 12 may be any implantable medical device known in the art or later developed, for delivering an electrical therapeutic stimulus to the patient. In various embodiments, the pulse generator 12 is a pacemaker, an implantable cardiac defibrillator, and/or includes both stimulation and defibrillation capabilities. The portion of the leads 14, 16 extending from the pulse generator 12 to the vascular entry site 54 are also located subcutaneously or submuscularly. The leads 14, 16 are each connected to the pulse generator 12 via proximal connectors. Any excess lead length, i.e., length beyond that needed to reach from the pulse generator 12 location to the desired endocardial or epicardial implantation site, is generally coiled up in the subcutaneous pocket near the pulse generator 12.

The electrical signals and stimuli conveyed by the pulse generator 12 are carried to electrodes at the distal ends of leads 14, 16 by one or more conductors extending through the leads 14, 16. The one or more conductors are each electrically coupled to a connector suitable for interfacing with the pulse generator 12 at the proximal end of the leads 14, 16 and to one or more electrodes at the distal end. In an MRI environment, the electromagnetic radiation produced by the MRI system may be picked up by conductors of the leads 14, 16. This energy may be transferred through the leads 14, 16 to the electrode in contact with the tissue, which may lead to elevated temperatures at the point of contact. The present invention relates to a flexible core assembly insertable into conductor lumen to increase the overall inductance of the conductor to reduce the amount of MRI induced energy that is transferred to the electrodes by the conductor.

Figure 2:
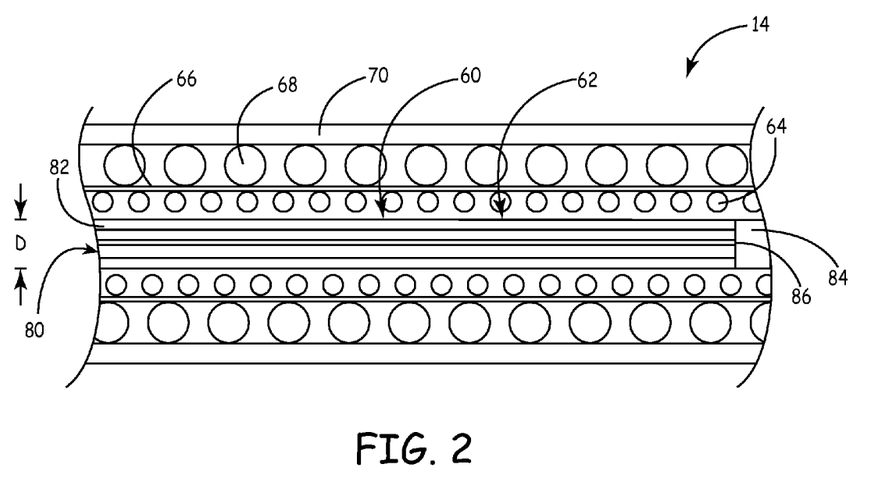
FIG. 2 is a cross-sectional view of a portion of the lead shown in FIG. 1 including an embodiment of a flexible core assembly disposed in a central lumen of the lead.

FIG. 2 is a cross-sectional view of a portion of the lead 14 shown in FIG. 1 including an embodiment of a flexible core assembly 60 disposed in a central lumen 62 of the lead 14. While the flexible core assembly 60 is shown associated with the lead 14, the flexible core assembly 60 may also be configured for use in association with lead 16. In the embodiment shown, the lead 14 includes an inner conductive coil 64, an intermediate insulation layer 66, an outer conductive coil 68, and an outer sheath 70.

The first conductive coil 64 and the second conductive coil 68 extend through the lead 14 and are adapted for connection to the pulse generator 12 at the proximal end of the lead 14, and to one or more electrodes at a distal end of the lead 14. In some embodiments, the first conductive coil 64 and the second conductive coil 68 are each coupled to a proximal connector at the proximal end of the lead 14. The connectors at the proximal end of the lead 14 are sized and shaped to interface with a connector block or other component of the pulse generator 12. The signals carried by the first conductive coil 64 and the second conductive coil 68 may be independently controlled by the pulse generator 12 such that different signals may be delivered to and/or received from the electrodes.

The inner conductive coil 64 comprises a helically-shaped conductive coil including one or more co-radial filars that are tightly wound together to form an inner conductor used to deliver electrical stimulus energy through the lead 14. In one embodiment, for example, the inner conductive coil 64 comprises a single filar. In other embodiments, the inner conductive coil 64 can include a greater number of filar strands.

In some embodiments, the inner conductive coil 64 has a hollowed configuration, including the central lumen 62 extending through the inner conductive coil 64 and adapted to receive a stylet or guidewire that can be used to facilitate implantation of the lead 14 within the body or to deliver the flexible core assembly 60 as will be described below. In certain embodiments, the inner conductive coil 64 can be fabricated by co-radially winding a number of wire filars about a mandrel having a diameter that is slightly greater than the diameter of the stylet or guidewire to be inserted in the lumen 62. To improve the torque characteristics and increase the inductance of the inner conductive coil 64, the wire filars can be tightly wound together during fabrication of the inner conductive coil 64 such that no gaps or spaces exist between the filar strands.

The outer conductive coil 68 is coaxially disposed about the inner conductive coil 64 and has a helically coiled configuration that extends along all or a portion of the length of the lead 14. In some embodiments, the outer conductive coil 68 has a single-filar construction formed from a single wound wire. In other embodiments, the outer conductor 68 has a multifilar construction formed from multiple, co-radially wound wire filars. In one embodiment, for example, the outer conductive coil 68 has a double-filar construction formed from two co-radially wound wire filars.

The outer conductive coil 68 can be spaced radially apart from the inner conductive coil 64, electrically isolating the outer conductive coil 68 from the inner conductive coil 64. In some embodiments, for example, the outer conductive coil 68 is electrically isolated from the inner conductive coil 64 so that the lead 14 can function as a multipolar lead. In certain embodiments, the intermediate insulation layer 66 is interposed between the inner conductive coil 64 and the outer conductive coil 68 to electrically isolate the conductive coils 64, 68 from each other. In some embodiments, for example, the intermediate insulation layer 66 may be comprised of, for example, silicone material, Teflon, expanded polytetrafluoroethylene (ePTFE), polytetrafluoroethylene (PTFE), ethylene tetrafluoroethylene (ETFE), or another suitable non-conductive material.

The flexible core assembly 60 comprises a magnetic core 80, an outer layer 82, and a positioning interface 84. A distal end of the core assembly 60 extends to or near the electrodes at the distal end of the lead 14. The core assembly 60 may extend from the electrodes through the lumen 62 to the proximal end of the lead 14, or may extend through only a portion of the lead 14. In some embodiments, the core assembly 60 has a length of up to about 125 cm. The core assembly 60 is sufficiently flexible to permit passage of the lead 14 through the patient's vasculature to the desired implantation position and to allow the lead 14 to flex with patient movements during implantation. The flexible core assembly 60 may be inserted into the lumen 62 in vivo or ex vivo, and may be configured for extraction from the lumen 62 after implantation.

The magnetic core 80 is a flexible length of material that operates to increase the inductance of the inner conductive coil 64 and outer conductive coil 68. This reduces the amount of electromagnetic energy that is transferred to the electrodes by the conductive coils 64, 68 when the lead 14 is exposed to an MRI environment, thereby reducing heating of the electrodes. In some embodiments, the magnetic core 80 has a substantially cylindrical shape when in an unflexed state.

In some embodiments, the flexible core assembly 60 further includes a reinforcement member 86 (also known as an axial support or tether) extending axially through the magnetic core 80. The reinforcement member 86 is configured to withstand tensile forces that typically occur after implantation of the lead 14 within the body. The reinforcement member 86 can be made from a variety of materials. In some embodiments, the reinforcement member 86 can be a polymeric monofilament made from polytetrafluoroethylene, ethylene tetrafluoroethylene, or high modulus silicone. In other embodiments, the reinforcement member 86 can be a polymeric multifilament braid or weave made from polyethylene terephthalate and/or other materials. In some embodiments, the reinforcement member 86 can be a polymeric tube such as a high modulus silicone tube, a polyethylene terephthalate tube, a biaxially-oriented polyethylene terephthalate tube, or a polyethylene terephthalate/silicone tube. In still further embodiments, the reinforcement member 86 can be a wire or stranded wire.

The magnetic core 80 has a saturation magnetization of at least the magnitude of the static field in the MRI system. For example, in some embodiments, the magnetic core 80 has a saturation magnetization of at least about 1.5 T. In other embodiments, the magnetic core 80 has a saturation magnetization of at least about 2.2 T. In further embodiments, the magnetic core 80 has a saturation magnetization of at least about 3.0 T. Example materials that may be used for the magnetic core 80 that are flexible and have a sufficiently high saturation magnetization include, but are not limited to, cobalt iron alloys such as Hyperco, Permendur, and Supermendur, cobalt nickel alloys, and nanomagnetic materials.

The magnetic core 80 is disposed within the outer layer 82 to isolate the magnetic core 80 from the inner conductive coil 64. In some embodiments, the outer layer 82 is comprised of a biocompatible and biostable material that is compatible with long-term implantation. Example materials that may be used for the outer layer 82 include, but are not limited to, ethylene tetrafluoroethylene (e.g., Teflon®, Tefzel®), polyimide, silicone, polyurethane, parylene C, and combinations thereof. The outer layer 82 may also include a lubricious coating that allows the core assembly 60 to be readily translated through the lumen 62. Furthermore, in some embodiments, the outer layer 82 may be fabricated with a radiopaque marker that assists locating the core assembly during implantation and extraction.

The core assembly 60 may be formed with the outer layer 82 around the magnetic core 80 in a variety of ways. For example, in some embodiments, the outer layer 82 is extruded over the magnetic core 80. In other embodiments, the magnetic core 80 is injection molded into a sheath or tube of outer layer material. In further embodiments, the outer layer 82 is formed around the magnetic core 80 using other techniques, such as solvent casting or vapor deposition.

The outer layer 82 is formed to minimally affect the flexibility of the core assembly 60 and to maximize the volume of magnetic material in the core assembly 60. To this end, the thickness of the outer layer 82 is minimized relative to the diameter of the core assembly 60. In addition, in some embodiments, the diameter of the magnetic core 80 and the thickness of the outer layer 82 are selected such that the total diameter D of the core assembly 60 is substantially equal to the inner diameter of the inner conductive coil 64. In one exemplary implementation, the inner conductive coil 64 has an inner diameter of about 0.022-0.024 inch (0.056-0.061 cm). In such embodiments, the outer layer 82 may have a thickness of less than about 0.001 inch (0.003 cm), with the remainder of the volume of the core assembly consumed by the magnetic core 80. This maximizes the volume of the magnetic core 80 while isolating the magnetic core 80 from the inner conductive coil 64 without having a substantial affect on the flexibility of the core assembly 60.

To increase the inductance of the inner conductive coil 64 and outer conductive coil 68, the core assembly 60 increases the relative permeability of the lumen 62 compared to the lumen 62 without the core assembly 60 disposed therein. An open lumen 62 has a relative permeability $\mu_r$ of about 1.0, since the open lumen 62 generally includes air inside the inner conductive coil 64. Thus, to increase the inductance of the inner conductive coil 64 and outer conductive coil 68, in some embodiments, the core assembly 60 has a relative permeability $\mu_r$ of greater than about 1.0. In some embodiments, the core assembly 60 has a relative permeability $\mu_r$ of greater than about 10. In other embodiments, the core assembly 60 has a relative permeability $\mu_r$ of greater than about 100.

Figure 3:
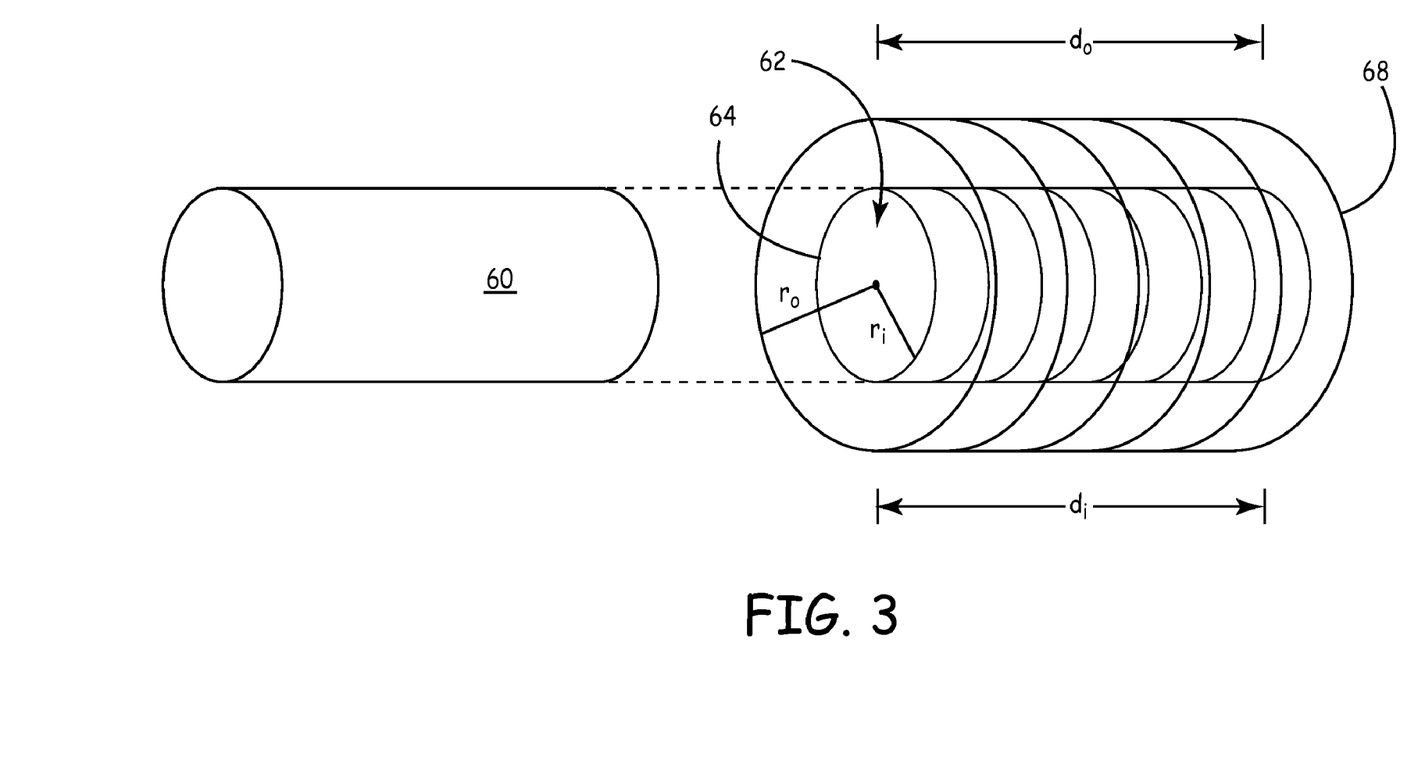
FIG. 3 is a diagram illustrating the effect of the flexible core material on the inductance of the inner and outer conductive coils.

FIG. 3 is a diagram for illustrating the effect of the core assembly 60 on the inductance of the inner conductive coil 64 and outer conductive coil 68. The inner conductive coil 64 has a radius $r_i$ and a length $d_i$ and the outer conductive coil 68 has radius $r_o$ and a length $d_o$. The lengths $d_i$ and $d_o$ are shown as being substantially equal, but in actual implementation the lengths $d_i$ and $d_o$ may be different. In addition, the inner conductive coil 64 includes a number of turns $N_i$ and the outer conductive coil 68 includes a number of turns $N_o$. In a lead 14 that does not include the core assembly 60 (i.e., has an open lumen 62), the inductance of the inner conductive coil 64 may be expressed as:

$$L_i = \frac{\mu_0 N_i^2 \pi r_i^2}{d_i}, \qquad (1)$$

and the inductance of the outer conductive coil 68 may be expressed as:

$$L_o = \frac{\mu_0 N_o^2 \pi r_o^2}{d_o}, \qquad (2)$$

wherein the permeability of the open lumen 62 and the space between the conductive coils 64, 68 are approximated to the permeability of free space (i.e., $\mu=\mu_0$).

When the core assembly 60 is inserted into the lumen 62, the relative permeability $\mu_r$ of the lumen 62 increases, thereby increasing the inductance of the conductive coils 64, 68. For simplicity, the following discussion does not consider the effect of the outer layer 82 on the relative permeability $\mu_r$ of the core assembly 60, since the effect of the thin outer layer 82 on the relative permeability $\mu_r$ of the core assembly 60 is relatively negligible. In particular, the inductance of the inner conductive coil 64 may be expressed as:

$$L_i = \frac{\mu_0 \mu_r N_i^2 \pi r_i^2}{d_i}, \qquad (3)$$

and the inductance of the outer conductive coil 68 may be expressed as:

$$L_o = \frac{(\mu_r \pi r_i^2 + \pi(r_o^2 - r_i^2))\mu_0 N_o^2}{d_o}, \qquad (4)$$

wherein the permeability of the space between the conductive coils 64, 68 is approximated to the permeability of free space (i.e., $\mu=\mu_0$). As is shown, the inductance of the inner conductive coil 64 and outer inductive coil 68 are linearly related to the relative permeability $\mu_r$ of the core assembly 60.

The positioning interface 84 (FIG. 2) provides a mechanism that a clinician can use to manipulate the core assembly 60 in the lumen 62. The core assembly 60 may be inserted into the lumen 62 before the lead 14 is implanted in the patient (ex vivo) or after the lead is implanted in the patient (in vivo). In some embodiments, the positioning interface 84 is configured to couple with a guidewire, stylet, or other guiding device during positioning of the core assembly 60 and to decouple with the guidewire, stylet, or other guiding device after the core assembly 60 is positioned. For example, the guidewire or stylet may include an expandable assembly at its distal end that is actuatable by the clinician at the proximal end that, when expanded, couples with the positioning interface 84 and, when retracted, decouples from the positioning interface 84. The positioning interface 84 may also include an expandable mechanism that secures the core assembly 60 with respect to the lead 14. The positioning interface 84 may be comprised of a biocompatible and biostable material. For example, in one exemplary implementation, the positioning interface 84 may be formed of a cobalt body with a silicone shell and a biocompatible exterior of ethylene tetrafluoroethylene (e.g., Teflon®, Tefzel®), polyimide, silicone, polyurethane, parylene C, or combinations thereof.

Figure 4:
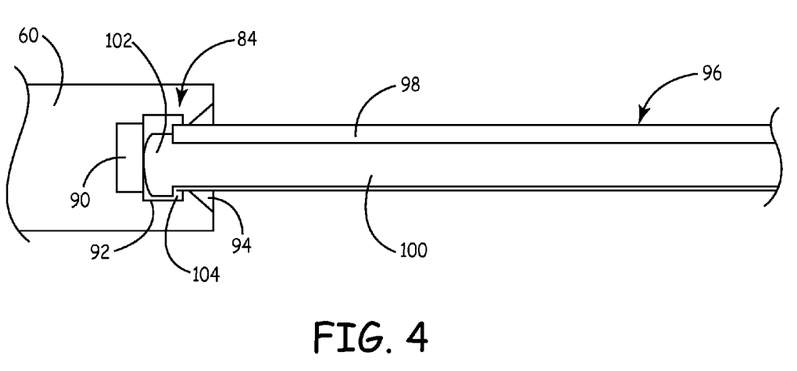
FIG. 4 is a cross-sectional view of a proximal end of the flexible core assembly interfaced with a stylet for implantation or removal of the flexible core assembly from the central lumen.

FIG. 4 is a cross-sectional view of a proximal end of the core assembly 60 including an embodiment of a positioning interface 84. The positioning interface includes an end cap 90, a retention opening 92, and a proximal entry opening 94. The proximal entry opening 94 is sized to receive the distal end of a stylet 96 and provide a path for the distal end of the stylet 96 into the retention opening 92. In some embodiments, the proximal entry opening 94 is tapered such that the width of the entry point at the proximal end is enlarged to facilitate positioning of the stylet 96 in the positioning interface 84. The narrow end of the tapered proximal entry opening 94 may have a width substantially similar to the width of the distal end of the stylet 96. The end cap 90 provides a structure that stops the distal end of the stylet 96 from further penetrating the core assembly 60. In some embodiments, the end cap 90 includes a radiopaque marker to assist the clinician in positioning and locating the core assembly 60.

When the distal end of the stylet 96 is located in the retention opening 92, the stylet 96 may be manipulated to expand the distal end of the stylet 96 and couple the stylet 96 with respect to the core assembly 60. For example, in the embodiment shown, the stylet 96 includes a first body element 98 and a second body element 100. A head 102 is located at the distal end of the second body element 100. The body element 98 has a distal end width substantially similar to the distal end of the tapered entry opening 94. The body elements 98, 100 are sized such that rotation of the body elements 98, 100 with respect to each other (e.g., by a clinician at the proximal end) causes the axes of the body elements 98, 100 to move with respect to each other. This causes the head 102 to move from aligned with the distal end of the body element 98 in the retracted position to offset from the distal end of the body element 100 in the expanded position. Thus, when the distal end of the stylet 96 is adjacent to the end cap 90, the clinician may rotate the body elements 98, 100 with respect to each other and to actuate the head from the retracted position to the expanded position. This moves the head 102 laterally within the retention opening 92. FIG. 4 shows the stylet 96 in the expanded position. In this configuration, the head 102 is secured between the end cap 90 and a lip interface 104 between the retention opening 92 and the proximal entry opening 94. Consequently, the clinician is able to manipulate the core assembly 60 in the lumen 62 for implantation, positioning, or extraction.

In summary, embodiments of the present invention relate to a medical device lead including an insulative lead body, outer and inner conductive coils, and a flexible core assembly. The outer conductive coil extends through the lead body and is coupled to a first electrode at a distal end of the outer conductive coil. The inner conductive coil extends coaxially with the outer conductive coil, is coupled to a second electrode at a distal end of the inner conductive coil, and includes a central lumen. The flexible core assembly is disposed in the central lumen and is comprised of a material that has a saturation magnetization of at least about 1.5 T and a relative permeability of greater than one. The flexible core assembly includes a positioning interface configured for manipulation of the flexible core assembly such that the flexible core assembly translates through the central lumen during insertion of the flexible core assembly into the central lumen and extraction of the flexible core assembly from the central lumen. The flexible core increases the overall inductance of the inner conductive coil, thereby reducing the amount of MRI induced energy that is transferred to the electrodes by the conductor.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A medical device lead comprising:
   an insulative lead body;
   an outer conductive coil extending through the lead body, the outer conductive coil coupled to a first electrode at a distal end of the outer conductive coil; and
   an inner conductive coil extending coaxially with the outer conductive coil, the inner conductive coil coupled to a second electrode at a distal end of the inner conductive coil, the inner conductive coil including a central lumen; and
   a flexible core assembly disposed in the central lumen, the flexible core assembly comprised of a material that has a saturation magnetization of at least about 1.5 T and a relative permeability of greater than one, the flexible core assembly including a positioning interface configured for manipulation of the flexible core assembly such that the flexible core assembly translates through the central lumen during insertion of the flexible core assembly into the central lumen and extraction of the flexible core assembly from the central lumen, the flexible core assembly further including a reinforcement member extending axially through the flexible core assembly.

2. The medical device lead of claim 1, wherein the positioning interface is on a proximal end of the flexible core assembly.

3. The medical device lead of claim 2, wherein the positioning interface is configured for connection to a distal end of a guiding device that allows manipulation of the flexible core assembly at a proximal end of the medical device lead.

4. The medical device lead of claim 3, wherein the positioning interface includes a tapered opening sized to receive the distal end of the guiding device.

5. The medical device lead of claim 1, wherein the flexible core assembly is substantially cylindrical in an unflexed state.

6. The medical device lead of claim 1, wherein the flexible core assembly is comprised of a nanomagnetic material.

7. A medical device lead comprising:
   a conductive coil extending through a lead body and including a proximal end, a distal end, and a central lumen; and
   a flexible core assembly disposed in the central lumen, the flexible core assembly comprised of a material that has a saturation magnetization of at least about 1.5 T and a relative permeability of greater than one, the flexible core assembly including a positioning interface configured for manipulation of the flexible core assembly such that the flexible core assembly translates through the central lumen during insertion of the flexible core assembly into the central lumen and extraction of the flexible core assembly from the central lumen, the flexible core assembly further including a reinforcement member extending axially through the flexible core assembly.

8. The medical device lead of claim 7, wherein the positioning interface is on a proximal end of the flexible core assembly.

9. The medical device lead of claim 8, wherein the positioning interface is configured for connection to a distal end of a guiding device that allows manipulation of the flexible core assembly at a proximal end of the medical device lead.

10. The medical device lead of claim 9, wherein the positioning interface includes a tapered opening sized to receive the distal end of the guiding device.

11. The medical device lead of claim 7, wherein the flexible core assembly is substantially cylindrical in an unflexed state.

12. The medical device lead of claim 7, wherein the flexible core assembly is comprised of a nanomagnetic material.

13. An assembly for increasing the inductance of a conductive coil in a medical device lead, the assembly positionable in a central lumen of the conductive coil, the assembly comprising:
   a flexible core comprised of a material that has a saturation magnetization of at least about 1.5 T and a relative permeability of greater than one, the flexible core including a reinforcement member extending axially through the flexible core; and
   a positioning interface coupled to a proximal end of the flexible core for manipulating the flexible core such that the flexible core translates through the central lumen during insertion of the flexible core into the central lumen and extraction of the flexible core from the central lumen.

14. The assembly of claim 13, wherein the positioning interface is configured for connection to a distal end of a guiding device that allows manipulation of the assembly at a proximal end of the medical device lead.

15. The assembly of claim 14, wherein the positioning interface includes a tapered opening sized to receive the distal end of the guiding device.

16. The assembly of claim 13, wherein the flexible core is substantially cylindrical in an unflexed state.

17. The assembly of claim 13, wherein the flexible core is comprised of a nanomagnetic material.

18. An assembly for increasing the inductance of a conductive coil in a medical device lead, the assembly positionable in a central lumen of the conductive coil, the assembly comprising:

a flexible core comprised of a material that has a saturation magnetization of at least about 1.5 T and a relative permeability of greater than one; and a positioning interface coupled to a proximal end of the flexible core for manipulating the flexible core such that the flexible core translates through the central lumen during insertion of the flexible core into the central lumen and extraction of the flexible core from the central lumen, wherein the positioning interface is configured for connection to a distal end of a guiding device that allows manipulation of the assembly at a proximal end of the medical device lead, and wherein the positioning interface includes a tapered opening sized to receive the distal end of the guiding device.

* * * * *